(12) United States Patent
Richardson

(10) Patent No.: US 6,314,405 B1
(45) Date of Patent: Nov. 6, 2001

(54) MEDICAL LOG APPARATUS AND METHOD

(76) Inventor: Donna L. Jung Richardson, 11890 Walbrook Dr., Saratoga, CA (US) 95070

(*) Notice: Subject to any disclaimer, the term of this patent is extended or adjusted under 35 U.S.C. 154(b) by 0 days.

(21) Appl. No.: 09/122,464

(22) Filed: Jul. 24, 1998

(51) Int. Cl.⁷ ................................................. G06F 17/60
(52) U.S. Cl. ............................. 705/3; 705/2; 600/300; 600/301
(58) Field of Search ............................. 705/2, 3; 600/300, 600/301, 483

(56) References Cited

U.S. PATENT DOCUMENTS

| | | | |
|---|---|---|---|
| 4,535,783 | * 8/1985 | Marangoni | 600/524 |
| 4,686,624 | 8/1987 | Blum et al. | |
| 5,307,263 | 4/1994 | Brown. | |
| 5,544,649 | * 8/1996 | David et al. | 600/301 |
| 5,553,609 | * 9/1996 | Chen et al. | 600/301 |
| 5,619,991 | * 4/1997 | Sloane | 600/300 |
| 5,642,731 | * 7/1997 | Kehr | 600/300 |
| 5,691,932 | 11/1997 | Reiner et al. . | |
| 5,722,999 | * 3/1998 | Snell | 607/32 |
| 5,778,882 | * 7/1998 | Raymond et al. | 600/513 |
| 5,993,400 | * 11/1999 | Rincoe et al. | 600/595 |

FOREIGN PATENT DOCUMENTS

406277178 * 10/1994 (JP).

OTHER PUBLICATIONS

Boos et al., "a new, light weight fetal telemetry system", Hewlett–Packard Journal, v46, n6, p82 (12), Dec., 1995.*

* cited by examiner

Primary Examiner—V. Millin
Assistant Examiner—Hani M. Kazimi

(57) ABSTRACT

An electronic, hand-held, easy-to-use, icon driven medical log that can be easily used by the elderly, children, the sick, the incapacitated and those with minimal computer skills. The medical log includes a first set of icons each representative of a different bodily condition and a second set of icons each representative of a different bodily location. A third set of icons is also provided to control the operation of the medical log. The medical log is initialized by programming the date and time into the device using the control icons. Once the medical log is initialized, a patient or a caretaker can make entries into the medical log by entering a bodily condition by selecting one of the first set of icons. The bodily location where the patient is experiencing discomfort is then entered into the medical log by selecting one of the second set of icons. The date and time the condition and bodily location was entered into the medical log is automatically stored in the log for later retrieval. Entries into the medical log can be made at prescheduled times each day or whenever the patient is experiencing discomfort. By consistently entering such information, an accurate log including the date, time, condition and location of the patient's ailments are recorded. Since information is entered into the log in a simple two-step operation using easy-to-understand icons, almost any patient or caretaker, regardless of their lack of computer skills or medical condition, can successfully use the present invention.

29 Claims, 8 Drawing Sheets

MEDICAL LOG APPARATUS AND METHOD

FIELD OF THE INVENTION

The present invention relates to a medical log, and more particularly, to an electronic, hand-held, easy-to-use, icon-driven medical log that can be intuitively and easily used by patients and caretakers, particularly those without any computer-related skills.

BACKGROUND OF THE INVENTION

Patients with certain medical conditions, diseases and/or chronic disorders are often required to make regular visits to a doctor. During such visits, the patient is typically required to recall and describe any problems, symptoms or ailments that occurred since the last visit. In response to the patient's input, the doctor keeps track of the patient's progress and often prescribes medication or some other form of treatment. Many patents, however, have difficulty accurately recounting this information to the doctor. Often patients and caretakers forget about the time and occurrence of a particular pain or ailment, or the patient is unable to communicate the information to the doctor because of a medical condition. A doctor may therefore fail to recognize a medical problem or misdiagnose and treat a different medical condition.

Medical logs have been used by patients and caretakers to help keep track and record a variety of health related incidences of a patient. U.S. Pat. Nos. 5,307,263 and 5,691,932 both disclose hand-held microprocessor-based health monitoring systems. With both of these devices, the patient or healthcare provider is required to manipulate a number of keys or switches to enter information and to cause a variety of symbols and icons to appear on a display. These devices, as a consequence, are not intuitive to use. As a result, certain patients such as the elderly, children, persons with little or no computer-related skills, or those too sick or incapacitated to learn may have difficulty using these devices.

Accordingly, an electronic, hand-held, easy-to-use, icon driven medical log that can be used by the elderly, children, the sick, the incapacitated, and those with minimal computer skills is needed.

SUMMARY OF THE INVENTION

The present invention relates to an electronic, hand-held, easy-to-use, icon driven medical log that can be easily used by the elderly, children, the sick, the incapacitated and those with minimal computer skills. The medical log includes a first set of icons each representative of a different bodily condition and a second set of icons each representative of a different bodily location. A third set of icons is also provided to control the operation of the medical log. The medical log is initialized by programming the date and time into the device using the control icons. Once the medical log is initialized, a patient or a caretaker can make entries into the medical log by entering a bodily condition by selecting one of the first set of icons. The bodily location where the patient is experiencing discomfort is then entered into the medical log by selecting one of the second set of icons. The date and time the condition and bodily location was entered into the medical log is automatically stored in the log for later retrieval. Entries into the medical log can be made at prescheduled times each day or whenever the patient is experiencing discomfort. By consistently entering such information, an accurate log including the date, time, condition and location of the patient's ailments are recorded. Since information is entered into the log in a simple two-step operation using easy-to-understand icons, almost any patient or caretaker, regardless of their lack of computer skills or medical condition, can successfully use the present invention.

BRIEF DESCRIPTION OF THE DRAWINGS

Referring to FIG. 1A, a medical log 10 according to the present invention is shown. The medical log 10 includes data entry locations 12a through 12d, a data display 14, an audio port 16 formed in the exterior casing 18 of medical log 10, input/output (I/O) port 20a, a power port 22a, a record control input 24 and a play control input 26. The data entry locations 12a–12d are used to control operation and enter data into the medical log 10. The display 14 is used to display data. The audio port 16 permits audio signals to readily pass in and out of the casing 18. The I/O port 20a is used to provide data communication signals to and from the medical log 10. The power port 22a is used to provide electrical power to the medical log 10. The record control input 24 is used to record a verbal message in the medical log 10. The play control input 26 is used to play a message recorded in the medical log 10.

Referring to FIG. 1B, a housing 30 used to house the medical log 10 is shown. The housing 30 includes a printer port 32, a modem port 34, a display 36, an I/O port 20b, a power port 22b, a power supply port 37, and data entry inputs 38a through 38c. The printer port 32 is used to send data stored in the housing 30 or medical log 10 to an external printer (not shown). The modem port 34 is used to send data stored in the housing 30 or medical log 10 to a remote location via a telephone line, the Internet, or some other type of data communication network. The display 30 is used to display data. The I/O port 20b, which is electrically coupled to the I/O port 20a when the medical log 10 is integrated in the housing 30, is used to communicate data signals to and from the medical log 10. The power port 22b, which is electrically coupled to the power port 22a when the medical log 10 is inserted into the housing 30, and provides electrical power to the medical log 10. The power supply port 37 is configured to be coupled to a steady power supply, such as an electrical outlet (not shown). In one embodiment, data entry inputs 38a through 38c are push button control inputs used to enter, print, transmit and download commands to the housing 30 respectively. In alternative embodiments the data entry inputs 38a–38c can be any type of data entry device such as a keyboard, touch screen display, or mouse.

Referring to FIG. 2 the data entry locations 12a–12d and the data display 14 of the medical log 10 are shown. The four data entry locations 12 includes a control location 12a, a patient condition location 12b, a patient symptoms location 12c, and a cardiovascular location 12d.

Figure 1A:
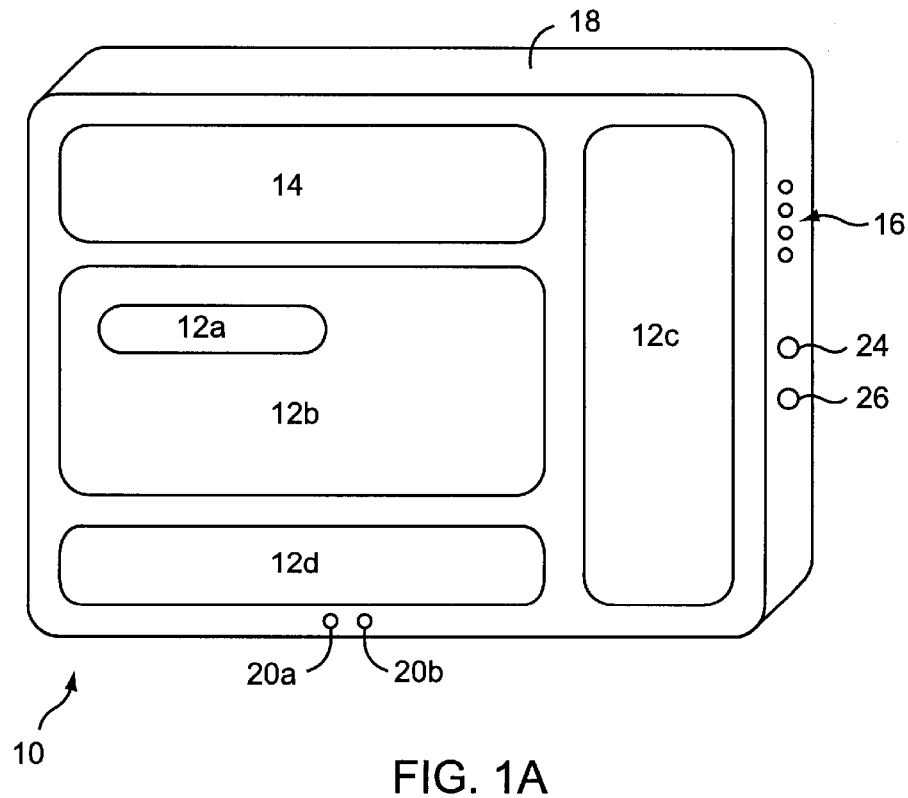
FIGS. 1A and 1B illustrate the medical log and corresponding housing unit of the present invention.
Figure 1B:
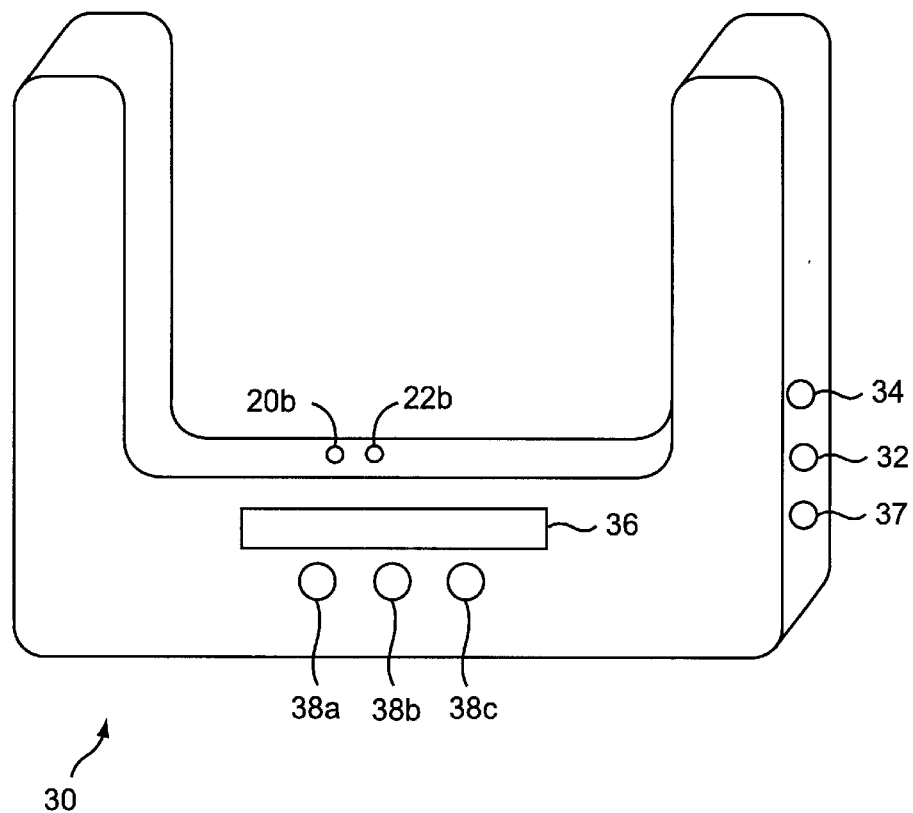
Figure 2:
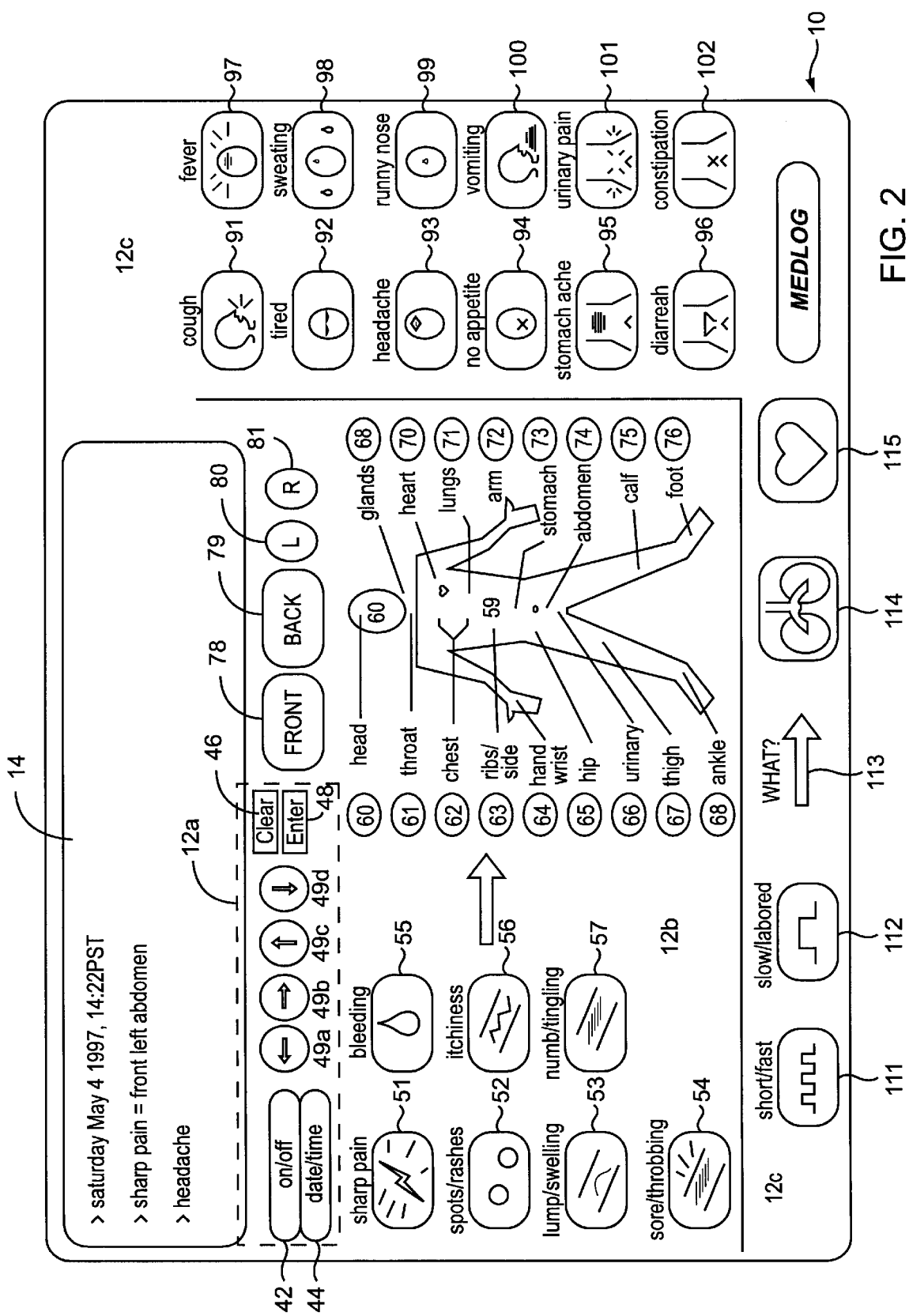
FIG. 2 illustrates the icon-driven data entry system and data output display of the medical log of the present invention.

The control location 12a includes the following icons: on/off 42; date/time 44; clear 46; enter 48; and direction arrows 49a, 49b, 49c and 49d pointing in the left, right, up and down directions respectively.

The patient condition location 12b includes the following icons: sharp pain 51; spots/rashes 52; lump/swelling 53; sore/throbbing 54; bleeding 55; itching 56; numb/tingling 57; "where?" arrow 58; patient's body 59; head 60; throat 61; chest 62; ribs/side 63; hand/wrist 64; hip 65; urinary 66; thigh 67; ankle 68; glands 69; heart 70; lungs 71; arm 72; stomach 73; abdomen 74; calf 75; foot 76; front 78; back 79; left 80; and right 81.

The patient symptom location 12c includes the following icons: cough 91; tired 92; headache 93; no appetite 94; stomachache 95; diarrhea 96; fever 97; sweating 98; runny nose 99; vomiting 100; urinary pain 101; and constipation 102.

The cardiovascular location 12d includes the following icons: short/fast 111; slow/labored 112; "what?" arrow 113; lungs 114; and heart 115.

Figure 3:
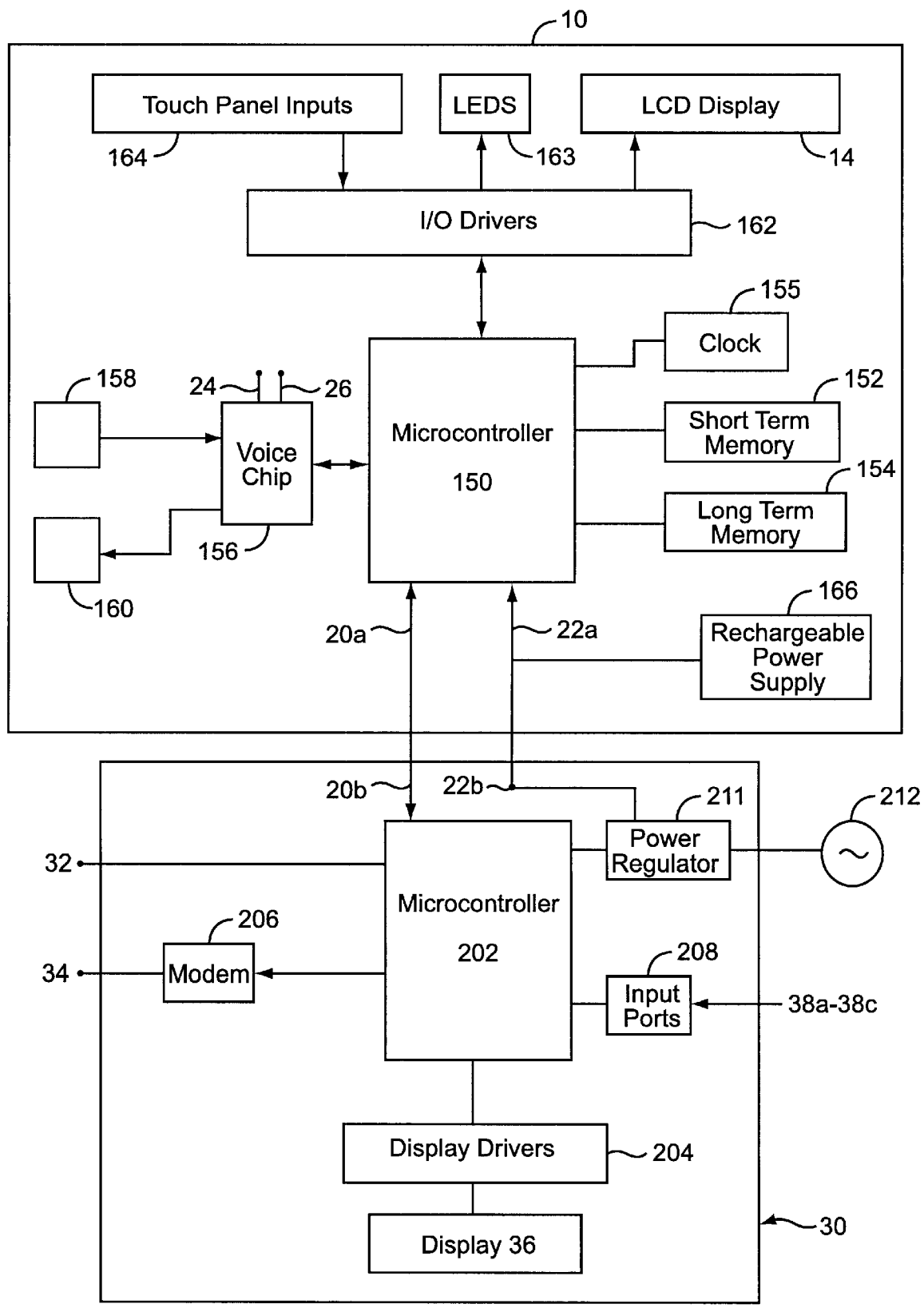
FIG. 3 is a functional block diagram of the medical log and housing unit of the present invention.

Referring to FIG. 3, a functional block diagram of the medical log 10 is shown. The medical log 10 includes a microcontroller 150, short term memory 152, long term memory 154, a clock chip 155, a voice chip 156, a microphone 158, a speaker 160, I/O drivers 162, LEDs 163, a plurality of touch panel inputs 164 corresponding to each of the icons in the control location 12a, patient location 12b (except "where ?" arrow 58), symptom location 12c, and cardiovascular location 12d (except "what?" arrow 113), display 14, a rechargeable power supply 166, I/O port 20a, and power port 22a.

In one embodiment, the short term memory 152, long term memory 154, clock circuitry on clock chip 155, I/O drivers 162, and interface for I/O port 20a and power port 22b are all integrated onto the microcontroller chip 150. The voice chip 156 records messages received by microphone 58 when the input 24 is pressed. The voice chip plays recorded messages on speaker 160 when the input 26 is pressed. The LEDs 163 are used to illuminate the "where?" arrow 58 and the "what?" arrow 113. In one embodiment the long term memory 154 is organized as a FIFO memory which is large enough such that out of date entries are over-written with current entries to the medical log 10.

Also referring to FIG. 3, a functional block diagram of housing 30 is shown. The housing 30 includes a microcontroller 202, display drivers 204 for driving display 36, a modem 206 coupled to modem port 34 and microcontroller 202, input ports 208 coupled to data entry inputs 38a–38c, printer port 32, a power regulator circuit 211, and an external power supply 212 coupled to the housing 30. The power regulator 211 provides a regulated power source to microcontroller 202. The power regulator 211 also provides a regulated power supply to the microcontroller 150 and rechargeable power supply 166 of the medical log 10 via ports 22b and 22a.

Figure 4:
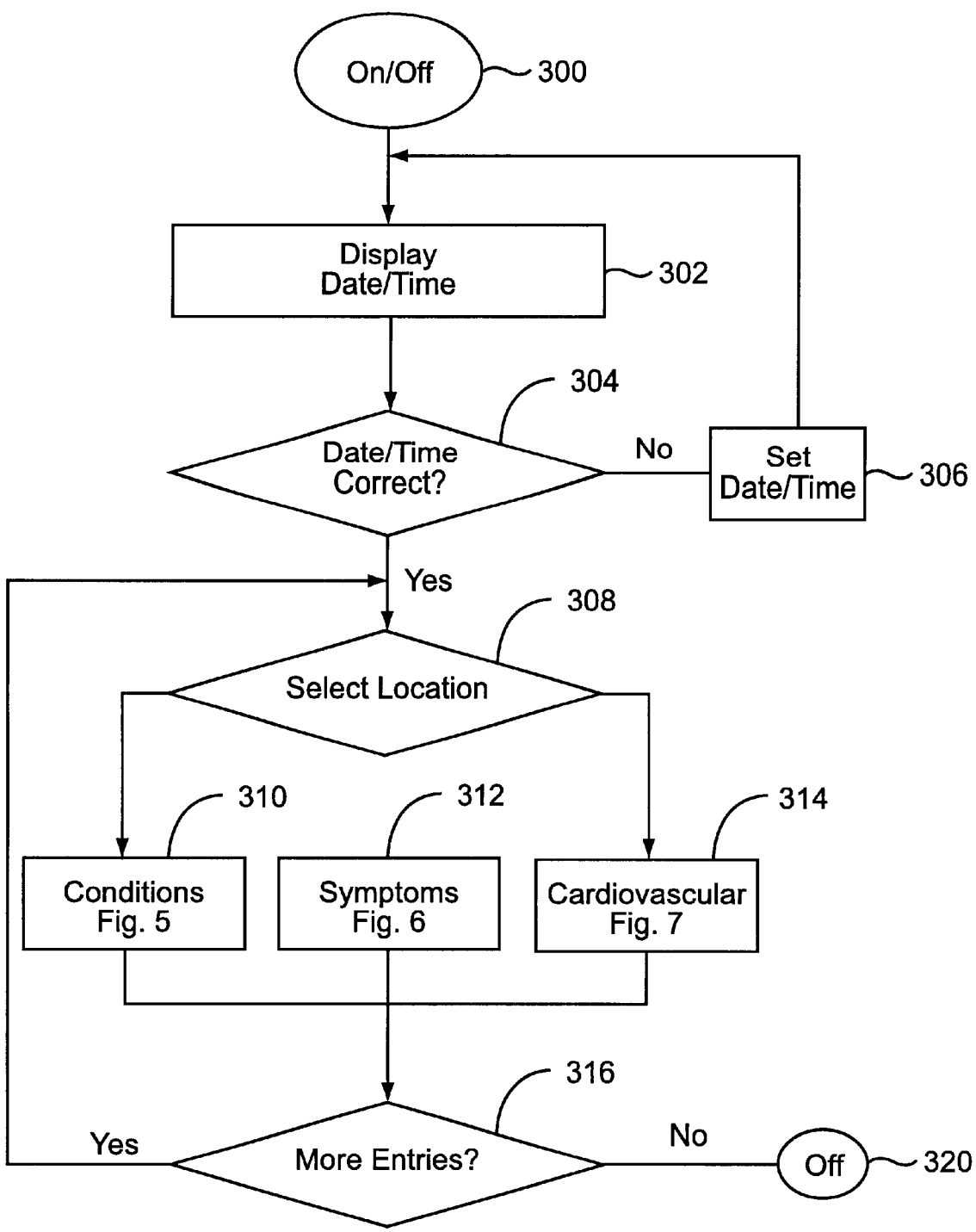
FIGS. 4–8 are flow charts illustrating the operation of the medical log and housing unit of the present invention.
Figure 5:
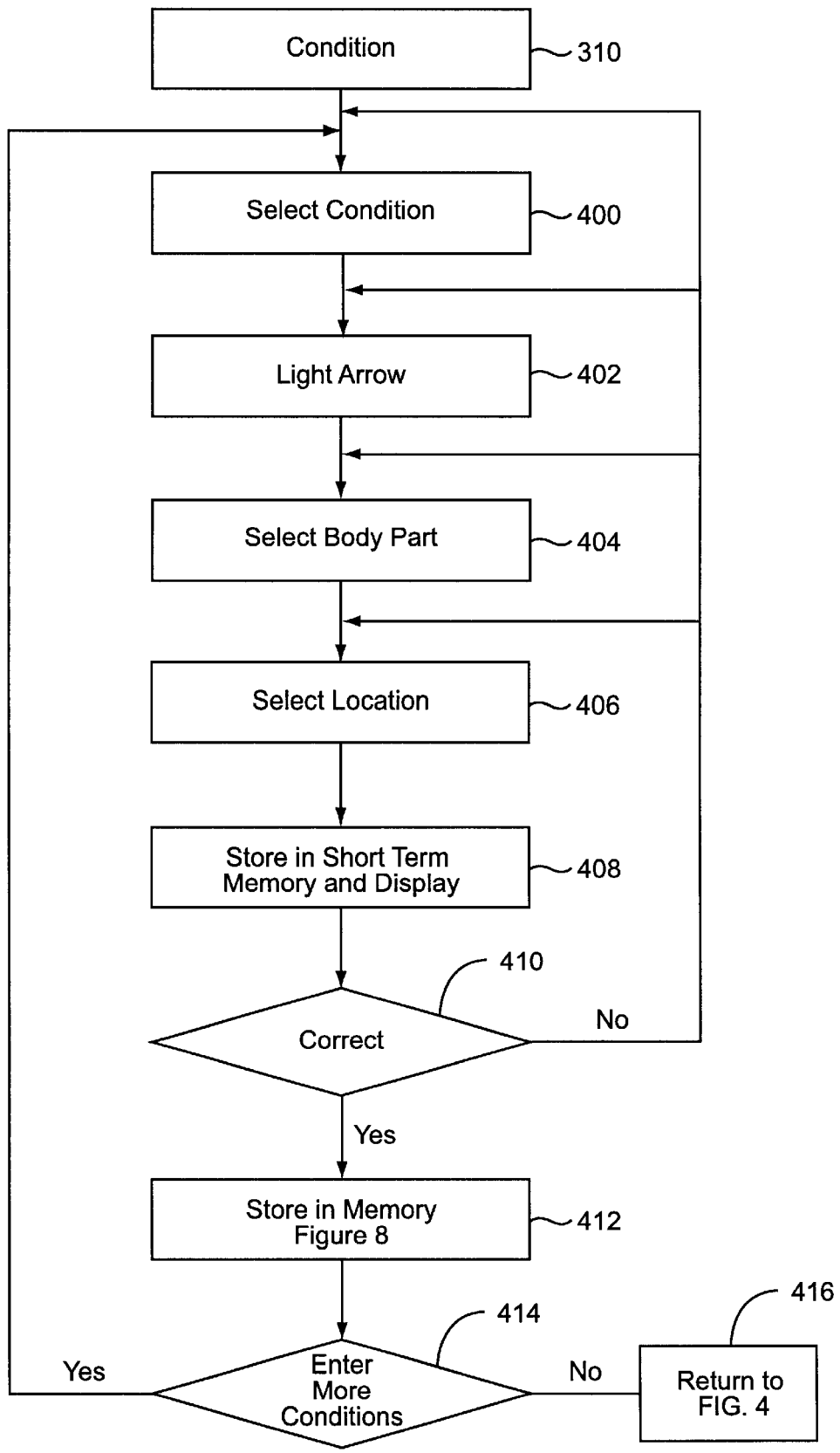
Figure 6:
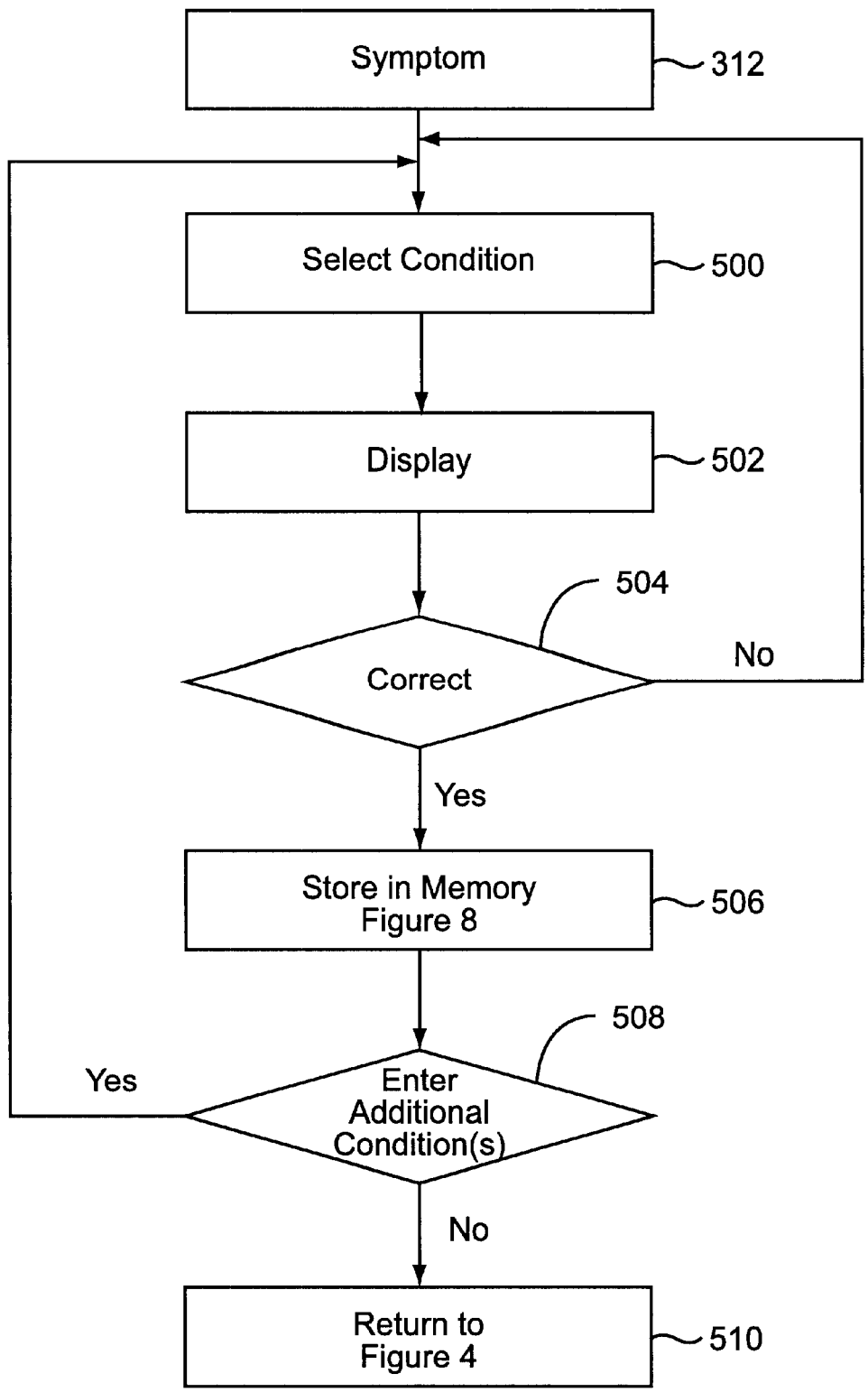
Figure 7:
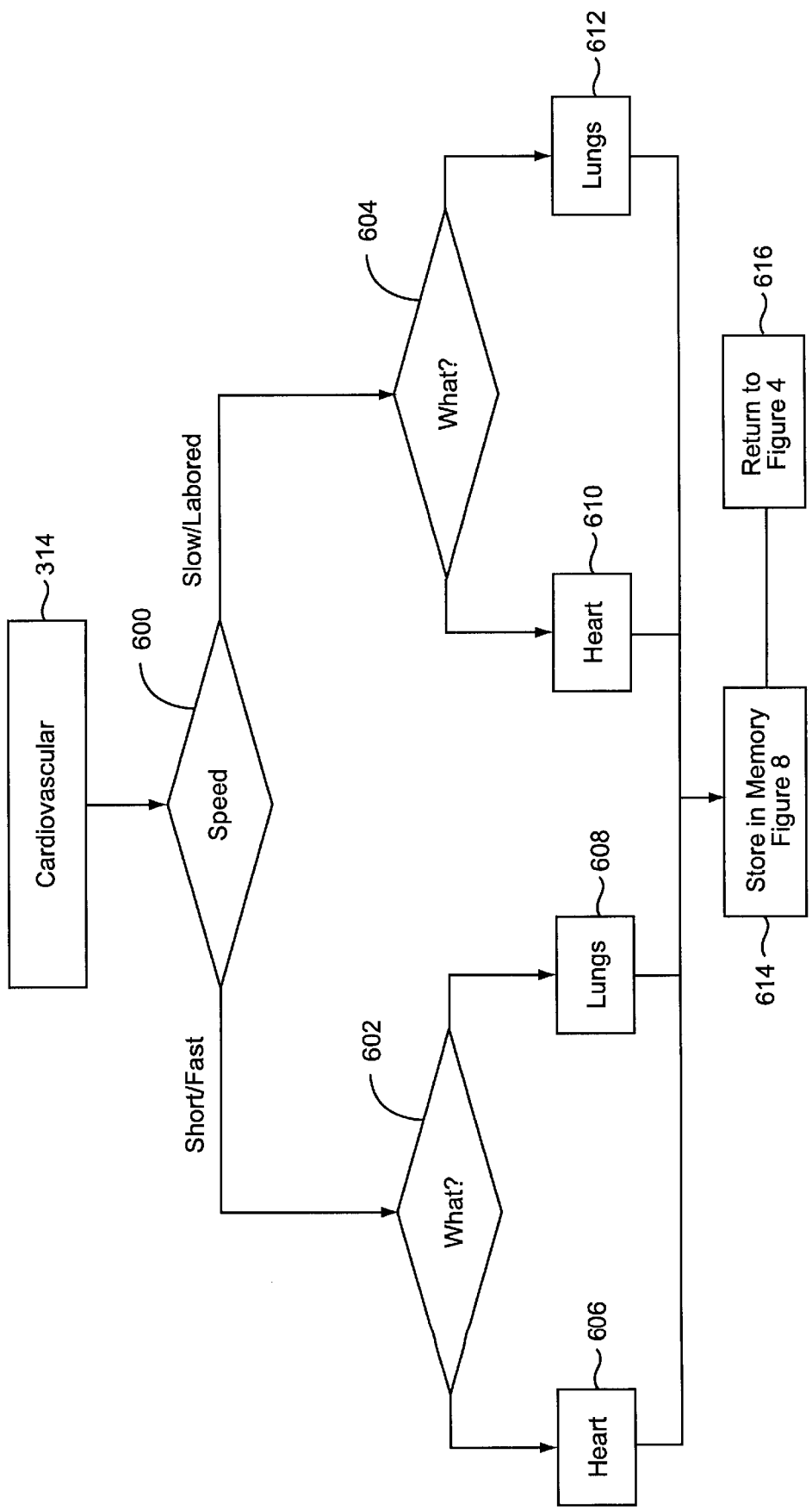
Figure 8:
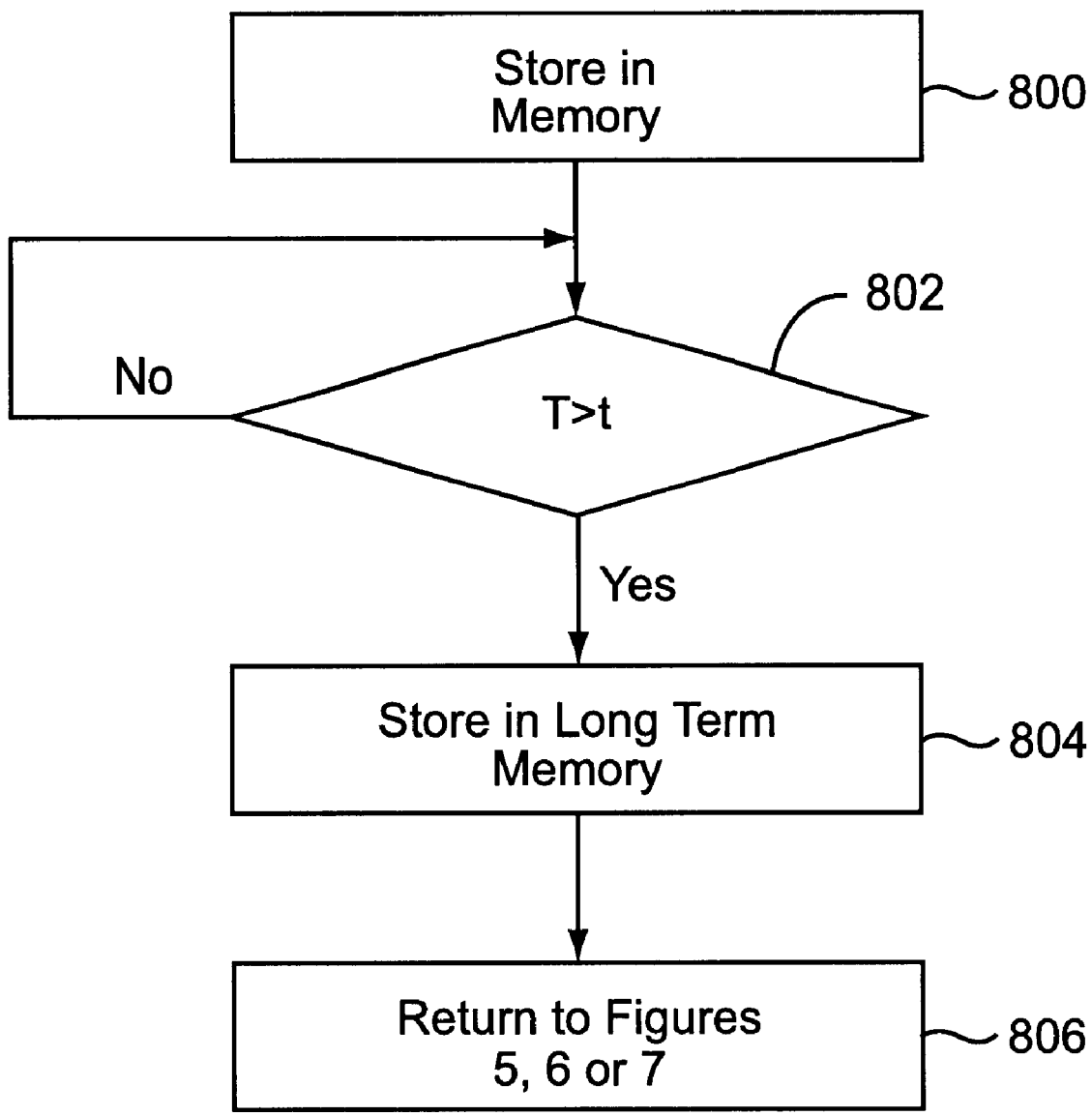

Referring to FIGS. 4 through 8, flow charts illustrating the operation of the medical log 10 is shown. Specifically, FIG. 4 shows the overall operation of the medical log 10. FIG. 5 illustrates the operation of the patient condition location 12b. FIG. 6 illustrates the operation of the patient symptom location 12c. FIG. 7 illustrates the operation of the cardiovascular location 12d. FIG. 8 illustrates how information is stored in the medical log 10. The flow chart of FIGS. 4–8 are described in detail below.

Referring to FIG. 4, operation of the medical log 10 is initiated by pushing the on/off icon 42 (oval 300). When the medical log 10 is turned on, the microcontroller 150 causes the date and time from the clock chip 155 to be displayed on display 14 (box 302). The patient or caretaker using the medical log then is required to check the displayed date and time with the actual date and time (decision diamond 304). If the displayed date and/or time are incorrect, then the correct date and/or time must be set (box 306). This is accomplished by pushing the date/time icon 44 and manipulating the direction arrows 49a, 49b, 49c and 49d. When the date/time icon is pushed, the month, date, year and time flashes on the display 14. The operator can then use the up arrow 49c to increment the month or the down arrow 49d to decrement the month. Each time either the arrows 49c or 49d is pushed, the month appearing on the display 14 is incremented or decremented respectively. When the correct month is set, then the right arrow 49b is pressed. This sets the month and stops the month from flashing on the display 14. The correct date is then set using the up direction arrow 49c and down direction arrow 49d. The year and time is set using the direction arrows 49a–49b in the same manner.

Once the date and time is set, the operator is required to select a location to make an entry into the medical log 10 (decision diamond 308). Data entries in the patient condition location 12b, the patient symptom location 12c and the cardiovascular location 12d are described below in relation to FIGS. 5, 6 and 7 (as indicated by boxes 310, 312 and 314 respectively). After an entry has been made, the operator decides if another entry is needed (decision diamond 316). If the decision is yes, then control is returned to the select location step (decision diamond 308). If the decision is no, then the data entry(ies) is stored in long term memory 154 (box 316) in accordance with the flow chart of FIG. 8. Thereafter the medical log 10 is turned off (oval 320). The medical log 10 may be turned off manually by pushing on/off icon 42. The microcontroller 150 is also programmed to automatically power down and turn the medical device 10 off after a period of inactivity (i.e. 5 or 10 minutes). This feature prevents the rechargeable power supply 166 from being drained and prevents the loss of data when the medical log 10 is inadvertently left on after use.

Referring to FIG. 5, the steps for data entry in the patient condition location 12b are illustrated. In patient condition location 12b (box 310), the operator is required to select a condition by pushing one of the icons 51 through 57 (box 400). The microcontroller 150 then causes the "where?" arrow 58 to illuminate (box 402). The arrow 58 reminds the operator to then select a body part. The operator then selects a body part by selecting one of the icons 60 through 76 (box 404). The operator may thereafter select a body location. This is accomplished by selecting one or more of the front, back, left, right icons 78 through 81 (box 406). The microcontroller 150 then stores the entries along with the date and time in short term memory 152 and displays the entered condition, body part and location on the display 14 (box 408). If the entry was incorrect, then the operator can push the clear icon 46 (decision diamond 410) which removes the entry from the short term memory 152. The operator can then reenter a condition icons 51 through 57, body part icons 60 through 76, and/or a body location icons 78 through 81. Once an entry has been made, it is stored in long term memory 154 in accordance with the flow chart of FIG. 8 (box 412). If the operator would like to enter another entry, the operator is required to select another icon 51 through 57 (decision diamond 414). Program control is thus returned (select conditions box 400) and the above steps are repeated. If no more condition entries are to be made, program control is returned to decision diamond 316 of FIG. 4 (box 416).

Referring to FIG. 6, the steps for data entry in the patient symptom location 12c is illustrated. In the patient symptoms location (box 312), the operator is required to select a symptom by pushing one of the icons 91–102 (box 500). The microcontroller 150 then displays the selected symptom on data display 14 (box 502). For example, if icon 97 is selected, then the condition "fever" is displayed. The operator then has the opportunity to delete the entry if it is incorrect (decision diamond 504). If the entry was incorrect, the operator is required to push the clear icon 46. This causes the entry to be erased from short term memory 152 and removed from the display 14. The operator may then make another symptom entry (box 500). On the other hand, if the entry was correct, then the entry remains in the short term memory 152 and is subsequently transferred to long term memory 154 in accordance with the steps described in FIG. 8 (box 506). The operator may also make additional symptom entries into the medical log 10 (diamond 508). If the operator wishes to make another entry, another symptom icon 91–102 is selected, program control returns to box 500, and the above steps are repeated. If no more entries are made, then program control is returned to decision diamond 316 of FIG. 4 (box 510).

Referring to FIG. 7, the steps for data entry in the cardiovascular location 12d are illustrated. In the cardiovascular location (box 314), the operator is required to select either short/fast or slow/labored respiratory activity by selecting either icon 111 or 112 respectively (decision diamond 600). The microcontroller then causes the "what?" arrow 113 to illuminate (decision diamonds 602 and 604). This reminds the operator to then select either the lungs by selecting icon 114 or heart 115 or both (boxes 606–612). The entry is then stored in short term memory 152 and subsequently long term memory 154 in accordance with the steps described in relation to FIG. 8 (box 614). Thereafter control is referred to decision diamond 316 of FIG. 4 (box 616).

Referring to FIG. 8, the steps for storing data in short term memory 152 into long term memory 154 is illustrated. Each entry (as described above in relationship to FIGS. 4–7) is initially stored in short term memory 152 (box 800). The microcontroller 150 then keeps track of the time (t) of the data entry. If the data entry is not cleared after a predetermined period (T) (decision diamond 802), then the entry along with date and time of the entry is stored in long term memory 154 (box 804). This process is repeated for each entry entered into short term memory 152. Once in long term memory 154, the entry can be later retrieved by downloading it to the housing unit 30.

The microcontroller 202 of the housing 30 controls the retrieval of information stored in the long term memory 154 of the medical log 10. The command for retrieving the data is provided to the microcontroller 202 by data entry input 38c. When the medical log 10 is in the housing 30 and the input 38c is selected, the microcontroller 202 prompts the microcontroller 150. In response the data stored in long term memory 154 is downloaded to the housing 30. Once the data is downloaded, it may be printed by selecting input 38a which sends the data to a printer via the printer port 32. The data entry input 38b causes the data stored in the housing 30 to be transmitted to a remote location via the modem 206. The microcontroller 202 controls the display 36 through driver 204 for the purpose of informing a user of certain events. For example, the display 36 may be used to indicate that the microcontroller 202 is communicating with the microcontroller 150, or that the microcontroller 202 is transmitting data to a printer or through the modem 206.

In one embodiment of the invention, a doctor prescribes that a patient (or the patient's caretaker) use the medical log 10 and housing 30 in the patients home, residence, or other location where the patient is staying. The patient or caretaker can then make daily entries into the medical log 10 or entries whenever the patient is bothered by some type of symptom or condition. The patient or caretaker can then periodically send the collected data to the doctor via the modem 206, or the medical log 10 can be brought to the doctor's office. The doctor can then insert the medical log 10 in a housing 30 located at the doctor's office where the data entries can be downloaded and printed.

In yet another embodiment, the voice chip 156 can be used to store and replay messages from a doctor or the patient. For example by selecting the record input 24, a doctor may record a message such as a certain medication must be taken a specific number of times a day. Thereafter the patient can replay the message on a regular basis by selecting the play input 26. This feature helps patients and caretakers follow a doctor's instructions. Alternatively, the patient or caretaker can use the voice chip 156 to record important messages regarding the condition of the patient. This information can then be replayed at the doctors office. The voice chip 156 therefore records and helps communicate important information which may otherwise be forgotten.

While the present invention has been described in relationship to the embodiment described in the accompanying specification, other alternatives, embodiments and modifications will be apparent to one skilled in the art. For example, the icons provided for the conditions location 12b, the symptom location 12c, and the cardiovascular location 12d are only exemplary, and any other type of icon representative of a bodily condition, location or symptom could be used. Additional functionality could also be added to the medical log of the present invention. For example, after the icon 97 is selected to record a patient's fever, the medical log 10 can be configured to enter and record the patient's temperature, using numerical keys (not shown) to perform the data entry operation. Alternatively, the medical log can be programmed to display "98.7" degrees after the icon 97 is entered. A caretaker could then use the up and down arrows 49c and 49d to cause the display to scroll up or down and to enter the patient's temperature into the log 10. Further, the medical log 10 can be configured to record medical information for more than one patient. This would require the user to program the medical log 10 for each patient and to inform the medical log 10 to identify the patient each time an entry is made. Again patients can be entered into the medical log and entries for individual patients can be entered into the log using the arrow keys, a keyboard (not shown) or other standard data entry means. The invention can also be implemented in software running on a standard computer, such as an IBM compatible PC, workstation, or a hand-held computer, such as the "Palm-Pilot" from 3COM Corporation, Milpitas, Calif. or other hand-held computer running Microsoft's "CE" or similar operating systems. In such embodiments, the software will cause the icons 42–115 to be displayed on the display unit of the computer. Icons are selected and operation of the device is controlled by use of either a touch-input screen, or by using the keyboard, mouse, or other input device in a known manner. It is intended that the specification only be exemplary, and that the true scope and spirit of the invention be indicated by the following claims.

What is claimed is:

1. A medical log for a patient, comprising:
    a memory;
    a first set of different icons each representative of a different bodily ailment, each ailment indicative of a variety of different conditions and/or symptoms that the patient may experience;
    a second set of icons each representative of a different bodily location;
    a third set of icons representative of control operations to control the operation of the medical log; and a first circuit, coupled to the memory, the first set of icons, the second set of icons, and the third set of icons, the first circuit configured to identify a selection of an icon pair including:
a selected one of the first set of icons representative of a selected bodily ailment; and
a selected one of the second set of icons representative of a selected body location,
the first circuit being further configured to store in the memory the specific time when the icon pair is selected, first information indicative of the selected one of the first set of icons and second information indicative of the selected one of the second set of icons so that when the specific time the patient was experiencing the selected bodily ailment at the selected bodily location can be logged into the medical log.

2. The medical log of claim 1, further comprising a display coupled to the first circuit, the first circuit further configured to display the bodily ailment and the bodily location when one of the first set of icons and one of the second set of icons are selected respectively.

3. The medical log of claim 2, wherein the first circuit is further configured to display on the display the time and date when the selected one of the first set of icons and the selected one of the second set of icons are selected.

4. The medical log of claim 1, where in the first set of icons includes icons representative of at least one of the following bodily ailment: sharp pain; spots/rashes; lump/swelling; sore/throbbing; bleeding; itching; numb/tingling; cough; tired; headache; no appetite; stomachache; diarrhea; fever; sweating; runny nose; vomiting; urinary pain; and constipation.

5. The medical log of claim 1, where in the second set of icons includes icons representative of at least one of the following bodily locations: patient's body; head; throat; chest; ribs/side; hand/wrist; hip; urinary; thigh; ankle; glands; heart; lungs; arm; stomach; abdomen; calf; foot; front; back; left; and right.

6. The medical log of claim 1, where in the third set of icons includes icons representative of at least on of the following control functions: on/off, clear, date/time, and control direction arrows.

7. The medical log of claim 1, further comprising a user visible pointer icon, coupled to the first circuit, the first circuit configured to activate the user visible pointer icon after one of the first set of icons is selected, the activated user visible icon providing a reminder for the user to select one of the second set of icons.

8. The medical log of claim 1, further comprising a housing unit configured to house the medical log.

9. The medical log of claim 8, wherein the housing unit and the medical log are configured to communicate through a data communication port.

10. The medical log of claim 8, wherein the housing unit is configured to provide electrical power to the medical log.

11. The medical log of claim 8, wherein the housing further includes a second circuit, configured to interact with the first circuit, the second circuit configured to direct the first circuit to download information including the time when selected ones of the first set of icons and the second set of icons were entered into the medical log.

12. The medical log of claim 11, wherein the second circuit further comprises a modem configured to transmit the information received from the medical log to a remote location.

13. The medical log of claim 11, wherein the second circuit further comprises print circuitry configured to transmit the information received from the medical log to a printer.

14. The medical log of claim 8, wherein the housing further includes a housing display to display status information during periods when the housing is receiving information from the medical log, printing the information, or transmitting the information to a remote location.

15. The medical log of claim 11, wherein the second circuit includes a microcontroller.

16. The medical log of claim 10, wherein the second circuit includes a power regulator configured to provide a voltage supply to the microcontroller.

17. The medical log of claim 1, wherein the first circuit includes a microcontroller.

18. The medical log of claim 1, wherein the memory includes a temporary memory configured to temporarily store the entered one bodily ailment and the entered one body location.

19. The medical log of claim 18, wherein the memory further includes a long term memory configured to store the entered one bodily ailment and the entered one body location stored in the temporary memory after a predetermined period of time T.

20. The medical log of claim 1, wherein the first circuit further comprises a clock circuit configured to keep track of the time when the selected bodily ailment and the body location is entered into the medical log.

21. The medical log of claim 1, wherein the first set of icons, the second set of icons and the third set of icons are electro-mechanically coupled to the first circuit.

22. The medical log of claim 2, wherein the display is a liquid crystal display.

23. The medical log of claim 7, wherein the user visible pointer icon is an light emitting diode.

24. The medical log of claim 1, wherein the first circuit further comprises a voice chip configured to record and playback messages.

25. The medical log of claim 1, wherein the first circuit further includes a rechargeable power supply configured to be recharged from a power source generated in a housing unit used to house the medical log.

26. The medical log of claim 1, wherein the first circuit further includes an output port configured to output the selected one bodily ailment and the one body location stored in the memory of the medical log to a housing unit configured to house the medical log.

27. The medical log of claim 1, further comprising a hand-held digital computer having a display screen programmed to display the first set of icons, the second set of icons, and the third set of icons on the display screen and further including processing circuitry including the first circuit.

28. The medical log of claim 1, further including selection circuitry, coupled to the first circuit, the selection circuitry configured to permit medical log information for different patients to be entered into the medical log.

29. The medical log of claim 4, further including a data entry element configured to permit a patient's temperature to be logged into the medical log.

* * * * *